United States Patent
Carchidi

Patent Number: 5,954,961
Date of Patent: Sep. 21, 1999

[54] BONE PARTICLE COLLECTION APPARATUS AND METHOD

[76] Inventor: Joseph E. Carchidi, 132 Samuel Ave., West Bridgewater, Mass. 02379

[21] Appl. No.: 08/741,378

[22] Filed: Oct. 29, 1996

Related U.S. Application Data

[60] Provisional application No. 60/007,136, Nov. 1, 1995.

[51] Int. Cl.⁶ .................................................. B01D 27/00
[52] U.S. Cl. ........................... 210/452; 210/455; 210/499
[58] Field of Search ..................................... 210/406, 446, 210/448, 451, 452, 455, 359, 499, 416.1, 416.2, 453, 389; 206/63.5

[56] References Cited

U.S. PATENT DOCUMENTS

| | | | |
|---|---|---|---|
| 1,199,350 | 9/1916 | Collin | 210/414 |
| 1,688,846 | 10/1928 | Andrews | 210/464 |
| 4,062,781 | 12/1977 | Strauss et al. | 210/446 |
| 4,701,259 | 10/1987 | Rosaen | 210/450 |
| 5,100,541 | 3/1992 | Kallenbach | 210/94 |
| 5,290,445 | 3/1994 | Buttery | 210/445 |

Primary Examiner—W. L. Walker
Assistant Examiner—Richard W. Ward
Attorney, Agent, or Firm—John A. Haug

[57] ABSTRACT

A bone particle collecting unit (30) has first (32) and second (34) interfitting housing members capturing a cylindrical screen basket assembly (64). Bone particle containing effluent from a surgical site is received through a port (40) in the first housing member (32) into the screen basket assembly (64). Suction is applied from a port (56) in the second housing member (34) to remove liquid which passes through the screen basket assembly. The screen basket assembly (64) includes a disc (66) which frictionally receives one end of a cylindrical screen (70) with the other end o the screen received about a rib (42) formed in the first housing member (32). Disc (66) of the screen basket assembly is received on guide ribs (58) to seat the assembly in the second housing member (34). After removing the screen basket assembly (64) from the housing members a plunger (86) can be inserted into the open end of the assembly to consolidate the bone particles and to expel the consolidated bone particles onto a collection surface (98).

4 Claims, 4 Drawing Sheets

BONE PARTICLE COLLECTION APPARATUS AND METHOD

This is a continuation of Provisional Application Ser. No. 60/007,136, filed Nov. 1, 1995.

FIELD OF THE INVENTION

This invention relates generally to surgical devices and more particularly to devices for collecting bone particles produced during various surgical procedures.

BACKGROUND OF THE INVENTION

It is conventional to use particles of bone obtained from bony sites during certain surgical procedures in order to fill post surgical bony defects elsewhere. For example, such procedures include, but are not limited to, dental implant surgery involving the mandible and maxilla and mastoid surgery such as the reconstruction of the posterior bony canal wall of the ear.

According to a prior art bone particle collecting device, a disposable cylindrical stainless steel screen having a longitudinal axis is mounted on the bottom wall of a cup shaped body. The longitudinal axis of the screen is disposed in vertical relationship with the bottom wall of the body and with an annular space formed around the cylindrical screen. A cover member has a cylindrical spindle depending downwardly from a top wall thereof centrally disposed relative to the side wall of the body. The spindle is arranged to fit within the opening at the top of the cylindrical screen. A tubular port fitting communicates with the interior of the screen by extending through a side wall of the spindle and the side wall of the cover member for attachment to a suitable tube. Another tubular port fitting communicates with the exterior of the screen by extending through the side wall of the cover member in communication with an annular space between the spindle member and the side wall of the cover member. The device is adapted to be attached to a suction line having an end adapted for placement at a surgical site being irrigated and with an opposite end attached to a suction source.

Although the device is effective in collecting bone particles in an amorphous mass, it is difficult to efficiently gather and handle the osseous material, particularly without wasting much of the material. Another limitation of the prior art device is that the device can only be sterilized by ethylene oxide. Additionally, the cylindrical screen ends of the prior art device are cut and easily fray thereby making reassembly at surgery a difficult task.

SUMMARY OF THE INVENTION

It is an object of the present invention to provide a bone collecting apparatus and method which overcome the above noted limitations of the prior art. Another object of the invention is the provision of an improved bone collecting apparatus and method which is inexpensive yet reliable and efficient.

Briefly, in accordance with the invention, a cylindrical first housing member has an end wall formed with a coaxially extending first tubular port fitting and a cylindrical rib extending from the end wall and being spaced from a side wall. A gasket receiving groove is formed about the periphery of the side wall of the first housing member adapted to be telescopically received in the outer distal portion of a cylindrical side wall of a second housing member. A disposable stainless steel cylindrical screen is closely received on a cylindrical hub portion of a disc to form a screen basket assembly. The opposite end of the screen is then closely received around the rib on the end wall of the first housing member. Both screen ends are preferably folded over to resist fraying and to allow multiple collections with the same screen during a surgical procedure. The first housing member and screen basket assembly are then inserted into the second housing member with the disc received on a plurality of base supports extending along the side wall to mount the base centrally spaced from the side wall of the second housing member. A second coaxially extending tubular port fitting extends through an end wall of the second housing member. The first port fitting communicates with the interior of the screen basket assembly and the second port fitting communicates with the exterior of the assembly. In use, the first and second tubular port fittings are attached to suction tubes and the bone particles are collected within the screen basket assembly by connecting the suction source to the surgical site being irrigated. Once sufficient bone particles have been collected suction is discontinued and the apparatus is disassembled by separating the housing members from each other. The screen basket assembly is then removed with the disc below and attached to the screen. The osseous material may be removed by spooning it out of the assembly or it may be consolidated to form a dense pancake like mass which is more easily handled. A plunger having a cylindrical head portion closely receivable in the cylindrical screen may be inserted into the open end of the screen basket assembly to compress the material within the screen basket assembly and force excess fluid through the screen. The screen basket assembly, with the plunger still in place, may be held horizontally or placed on a table top and excess moisture may then be forced through the screen. The screen is then held generally vertically (the longitudinal axis in a vertical position) over a collection surface, such as a bowl, and the plunger is then pushed down to free the consolidated osseous particulate material free of the screen either with the disc removed separately or atop the disc. The collection device can then be easily reassembled.

Additional objects and features of the invention will be set forth in part in the description which follows and in part will be obvious from the description. The objects and advantages of the invention may be realized and attained by means of the instrumentalities, combinations and methods particularly pointed out in the appended claims.

BRIEF DESCRIPTION OF THE DRAWINGS

The accompanying drawings, which are incorporated in and constitute a part of the specification, illustrate a preferred embodiment of the invention and, together with the description, serve to explain the objects, advantages and principles of the invention. In the drawings.

DETAILED DESCRIPTION OF THE PREFERRED EMBODIMENTS

Figure 1:
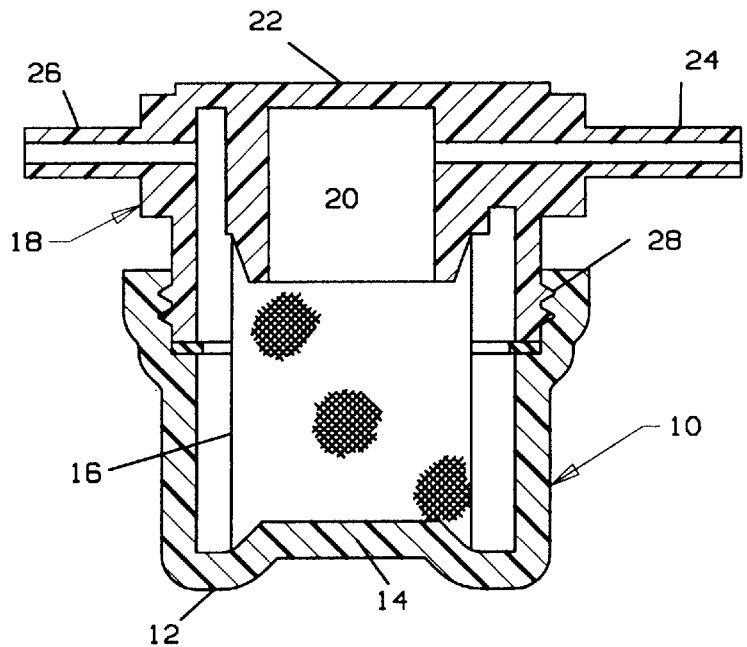
FIG. 1 is a cross sectional view of a prior art bone particle collection device.

With regard to FIG. 1, a prior art bone particle collecting device is shown comprising a cylindrical cup shaped body 10 having a bottom wall 12 formed with a raised centrally located boss 14 which serves as a seat for a disposable cylindrical screen 16. A cylindrical cover member 18 has a cylindrical wall 20 depending downwardly from a top wall 22 which forms a spindle received in the opening of the upper end of screen 16. A first tubular port fitting 24 extends horizontally from second body member 18 and communicates with a cavity formed by wall 20 and the interior of screen 16. A second tubular port fitting 26 extends horizontally from second body member 18 in the opposite direction and is in communication with an annular open space around wall 20 and screen 16. Body members 10 and 18 are attached to one another by a threaded section 28. The device is connected to a suction line used in irrigating a surgical site in order to collect bone particles by filtering the effluent. However, it is difficult to harvest the bone dust from the device in an efficient manner and without wasting osseous material. In order to harvest the osseous material body member 10 is unscrewed and separated, along with screen 16, from body member 18. A scoop of some sort is then used to gather the filtered material, however, the material is still amorphous and difficult to handle and a significant percentage of the filtered osseous residue is generally lost.

Figure 2:
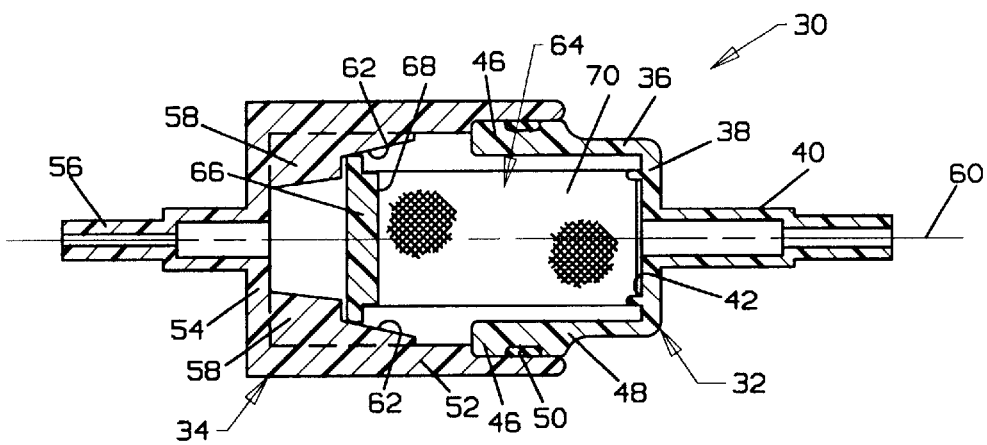
FIG. 2 is a cross sectional view of an improved bone particle collecting device made in accordance with the invention.

As will be described below, an improved osseous particle collector made in accordance with the invention provides an efficient collection apparatus which overcomes the above noted limitations of the prior art. With particular reference to FIG. 2, a collection unit 30 comprises first and second interfitting, generally cylindrical housing members 32, 34. Housing member 32 has a cylindrical side wall 36 extending from an end wall 38. A first tubular port fitting 40 extends through end wall 38 within the area defined by circular rib 42 extending inwardly from end wall 38. Rib 42 serves as a screen basket assembly seat, as will be explained below. Cylindrical side wall 36 is formed with a groove 44 formed around its outer periphery between two land portions 46, 48 at the distal free end of wall 38 for reception of a flexible sealing gasket 50.

Figure 2A:
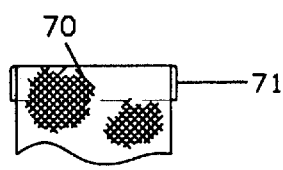
FIG. 2a is a broken away view of a portion of a screen used in the FIG. 2 device.

Housing member 34 has a generally cylindrical side wall 52 extending from an end wall 54. A second tubular port fitting 56 extends through end wall 54. Side wall 52 is formed with a plurality of screen basket assembly guide ribs 58 extending to end wall 54 from a location along the side wall intermediate its length. Ribs 58 taper inwardly toward the longitudinal axis 60 in a direction going toward end wall 54 forming a first tapered guide surface 62 having a selected length extending between first and second ends. A screen basket assembly 64 comprises a disc 66 formed with a screen seating boss 68 which frictionally mounts thereon one end of a cylindrical screen 70. Preferably, each end of screen 70 is folded over on itself as shown at 71 in FIG. 2a to resist fraying and to allow multiple collections, involving repeated assembly and disassembly, using the same screen during a given surgical procedure. The screen basket assembly is inserted into housing member 32 with the opposite end of screen 70 frictionally received around seating rib 42. The distal free end of side wall 36 of housing member 32 is then telescopically inserted into the distal free end of side wall 52 of housing member 34. Disc 66 of the screen basket assembly engages with tapered guide surface 62 at a location intermediate to the ends of the selected length maintaining the basket assembly in a selected centered position as seen in FIG. 2. Screen 70 is preferably formed of stainless steel having appropriate sized interstices, such as 80 mesh which has been found to be suitable. As seen in FIG. 2, the longitudinal axes of tubular port fittings 40, 56, housing members 32, 34 and screen 70 are all coaxial thereby forming an efficient path for effluent flow into screen basket assembly 64 through port fitting 40 and removal of excess liquid through the annular space around screen 70 and into port fitting 56. The coaxial feature of the port fitting and housing members also results in a configuration which is easily handled for attachment and detachment of suction tubes and the like. Unit 30 is formed of materials which can be cold sterilized or can be autoclaved.

Figure 3:
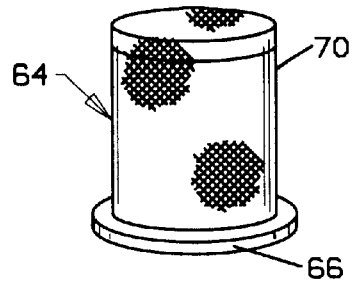
FIG. 3 is a perspective view of a screen basket assembly comprising a cylindrical screen mounted on a support base.
Figure 4:
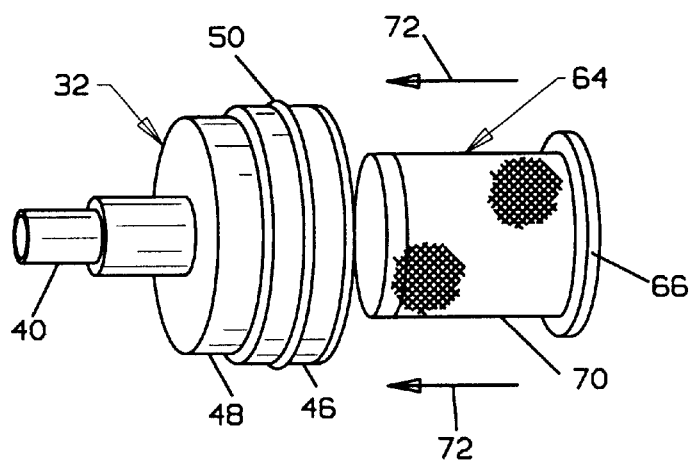
FIG. 4 is a perspective view of the FIG. 3 screen basket assembly being placed on a screen receiving seating surface of a first housing member.
Figure 5:
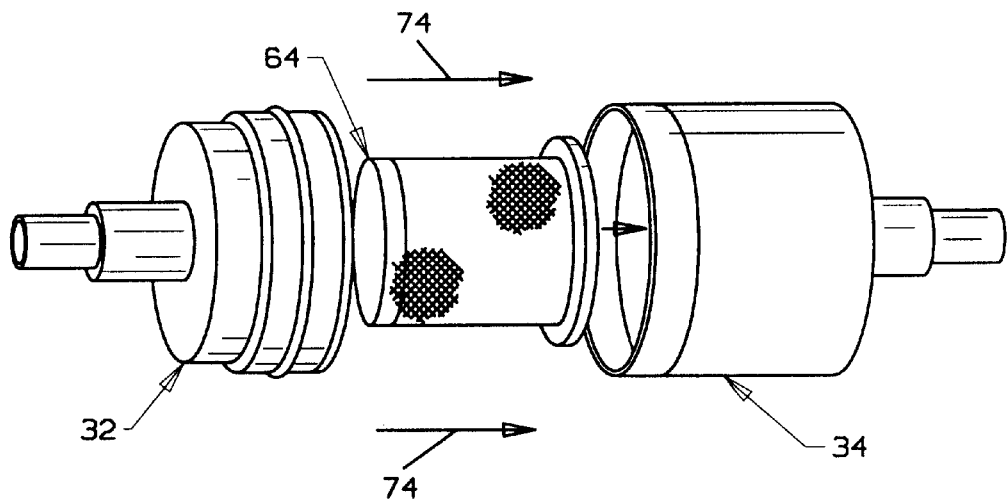
FIG. 5 is a perspective view of the first housing member and screen basket assembly being inserted into a second housing member.
Figure 6:
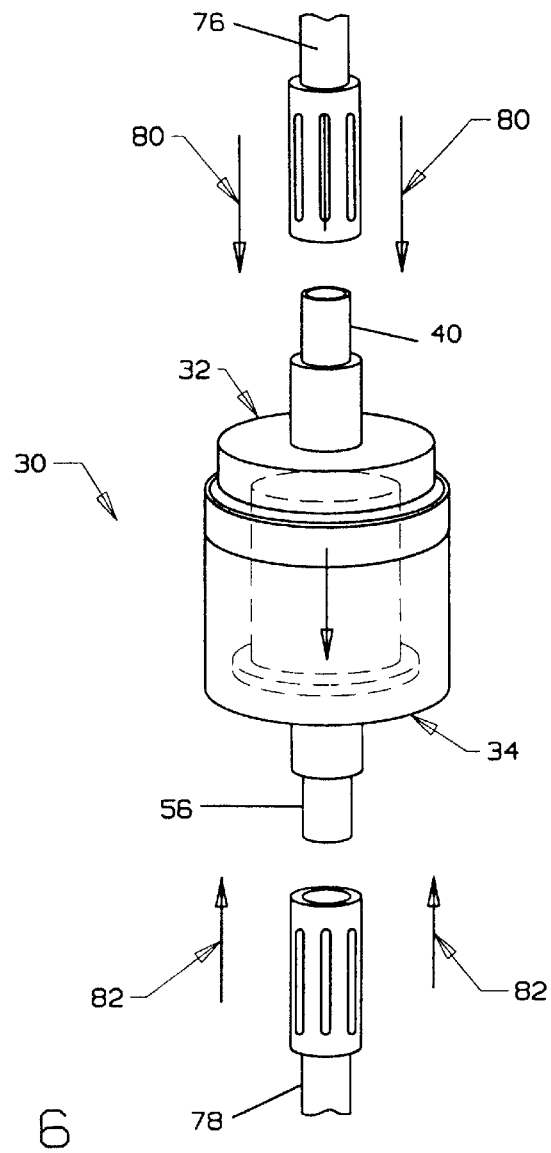
FIG. 6 is a perspective view of the bone collecting apparatus of FIG. 2 being connected to suction tubing.
Figure 7:
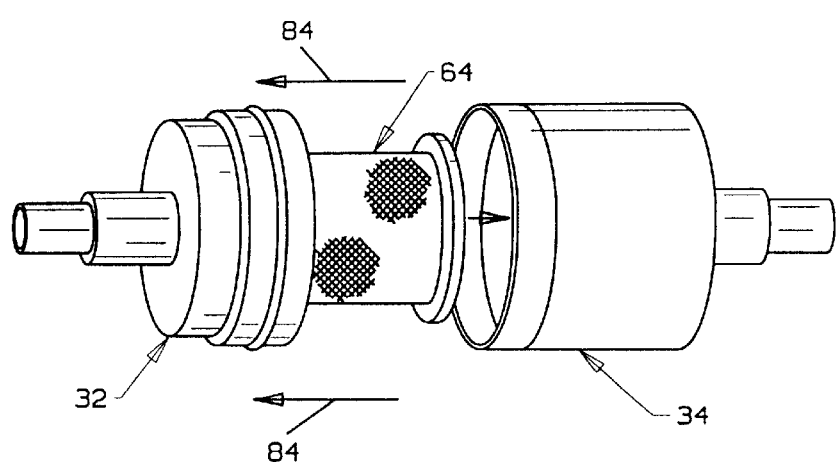
FIG. 7 is a perspective view similar to FIG. 5 but showing the apparatus being disassembled.
Figure 8:
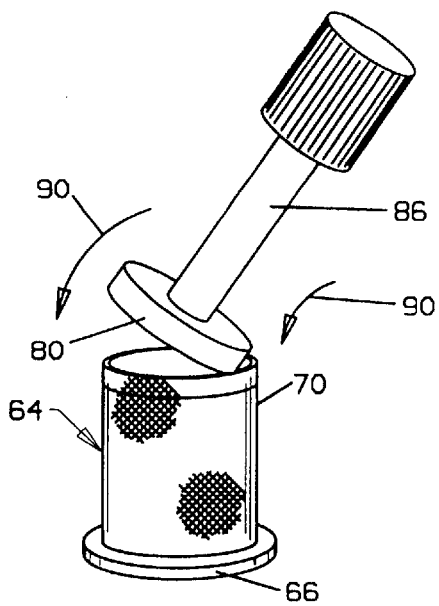
FIG. 8 is a perspective view of a plunger about to be inserted into the screen basket assembly.

Unit 30 is assembled by placing one end of screen 70 on disc 66 as shown in FIG. 3 to form a screen basket assembly which in turn is inserted into housing member 32 as indicated by arrows 72 in FIG. 4. Housing member 32 is then snapped into housing member 34 as denoted by arrows 74 in FIG. 5. Suitable suction tubes 76, 78 are then connected to port fittings 40, 56 respectively as noted in FIG. 6 by arrows 80, 82 respectively. Tube 78 is connected to a suction source to create a partial vacuum and tube 76 is placed at the surgical site. After sufficient bone has been collected, tubing 76 can be flushed with sterile saline in order to collect remaining bone particles. The unit can then be disassembled as indicated by arrows 84 in FIG. 7, separating housing member 32 from housing 34. Screen basket assembly 64 is then removed from housing member 32 being careful not to remove disc 66 from screen 70.

Figure 9:
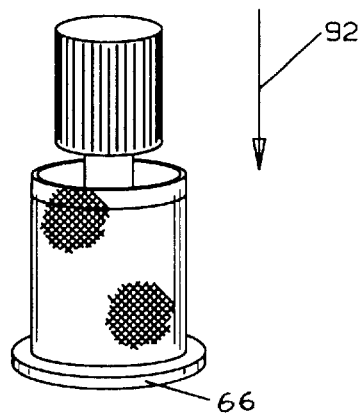
FIG. 9 is a perspective view showing the plunger depressed to compress the collected osseous particulated material.
Figure 10:
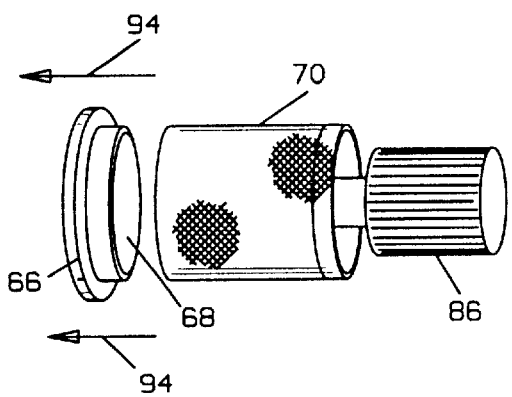
FIG. 10 is a perspective view showing the removal of the support disc from the screen basket assembly.
Figure 11:
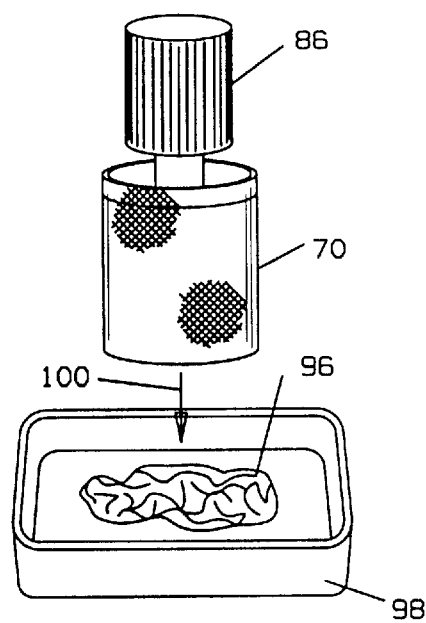
FIG. 11 is a perspective view showing placement of the consolidated osseous particulate material on a collection surface.

The osseous material within the screen basket assembly can be used in a wet, amorphous form by spooning it out of the screen basket assembly or it can be condensed into an easier to handle pancake form as shown in FIGS. 8–11. A plunger 86 having a cylindrical head 88 having a diameter selected to be closely receivable within the cylindrical space defined by screen 70 is inserted into the circular opening as indicated by arrows 90 in FIG. 8. Plunger 86 is preferably formed of biocompatible material such as titanium or a titanium alloy. The plunger is moved toward disc 66 as shown in FIG. 9 by arrow 92 to expel excess fluid through the interstices of the screen to form the pancake configuration. The screen basket assembly may be held with the longitudinal axis in a generally horizontal position and the disc may then be removed as indicated by arrows 94 in FIG. 10. Finally, the pancake configuration mass 96 of osseous material is freed from screen 70 by pushing down on the plunger while holding the screen generally vertically over a suitable collection surface, such as a titanium bowl 98 as shown by arrow 100 in FIG. 11. If desired, disc 66 need not be removed separately but can be removed with mass 96 by pushing down on plunger 86 over the collection surface.

Although the invention has been described with regard to a specific preferred embodiment thereof, variations and modifications will become apparent to those skilled in the art. It is, therefore, the intention that the appended claims be interpreted as broadly as possible in view of the prior art to include all such variations and modifications.

What is claimed:

1. Bone particle collecting apparatus comprising:

first and second housing members, the first housing member having an end wall, a first generally circular screen receiving seating surface extending from the end wall, an opening formed in the end wall within the circular screen receiving surface, the second housing member having an end wall and a side wall extending therefrom forming a screen receiving cavity, the second housing member having a screen basket assembly seat spaced from the end wall comprising a plurality of generally axially extending guide ribs attached to the side wall and having a tapered outer surface extending in a straight line along a selected length from a first end to a second end, the surface coming closer to the side wall as the distance from the end wall increases, an opening formed in the end wall, and a screen basket assembly comprising a disc having an outer peripheral edge and a second generally circular screen receiving seating surface, a generally cylindrical screen having first and second ends, the first end of the screen frictionlally and removably received on the second screen receiving seating surface and the first housing member coupled to the second housing member with only the outer peripheral edge of the disc engaging the tapered outer surface of the at least one of the guide ribs at a point intermediate to the first and second ends.

2. Bone particle collecting apparatus according to claim 1 in which the generally cylindrical screen has a longitudinal axis and the first and second housing members are generally cylindrical having longitudinal axes which are coaxial with each other and with the longitudinal axis of the screen the first housing member is coupled to the second housing member and with the screen basket assembly received in the housing members.

3. Bone particle collecting apparatus according to claim 1 in which the screen is formed of 80 mesh stainless steel.

4. Bone particle collecting apparatus according to claim 1 in which the cylindrical screen comprises a wire mesh screen having a main body portion in which the first and second ends are folded over into direct engagement with the main body portion to prevent fraying.

* * * * *